United States Patent [19]
Oda et al.

[11] Patent Number: 5,750,368
[45] Date of Patent: May 12, 1998

[54] PROCESS FOR PRODUCING A SUBSTANCE

[75] Inventors: Hideki Oda; Satoshi Nakagawa, both of Machida; Hideharu Anazawa, Tokyo, all of Japan

[73] Assignee: Kyowa Hakko Kogyo Co., Ltd., Tokyo, Japan

[21] Appl. No.: 715,249

[22] Filed: Sep. 19, 1996

Related U.S. Application Data

[63] Continuation of Ser. No. 314,297, Sep. 30, 1994, abandoned.

[30] Foreign Application Priority Data

Oct. 1, 1993 [JP] Japan ..................... 5-246478

[51] Int. Cl.$^6$ ............. C12P 21/02; C12P 19/30; C12P 19/34; C12N 1/21
[52] U.S. Cl. .................... 435/69.1; 435/252.33
[58] Field of Search ............. 435/252.3, 252.33, 435/69.1

[56] References Cited

FOREIGN PATENT DOCUMENTS 0 316 229 A1  5/1989  European Pat. Off. .
0316229       5/1989  European Pat. Off. .

OTHER PUBLICATIONS

Applied Biochemistry and Biotechnology, vol. 39/40, pp. 667–685, 1993, H.G. Lawford, et al., "Production of Ethanol From Pulp Mill Hardwood and Softwood Spent Sulfite Liquors By Genetically Engineered *E. coli*".

Applied Biochemistry and Biotechnology, vol. 34/35, pp. 185–204, 1992, H.G. Lawford, et al., "Effect of Acetic Acid on Xylose Conversion to Ethanol By Genetically Engineered *E. coli*".

Peter Landwall, et al., "Removal of Inhibitors of Bacterials Growth by Dialysis Culture", Journal of General Microbiology, vol. 103, pp. 345–352, 1977.

Youl Lark Lee, et al., "High Cell Density Culture of a Recombinant *Escherichia coli* Producing Penicillin Acylase in a Membrane Cell Recycle Fermentor". Biotechnology and Bioengineering, vol. 36, pp. 330–337, 1990.

Toru Matsui, et al., "Pressurized Culture of *Escherichia coli* for a High Concentration", Agric. Biol. Chem., vol. 53, pp. 2215–2120, 1989.

J.C. Diaz–Ricci, et al., "Effect of Alteration of the Acetic Acid Synthesis Pathway on the Fermentation Pattern of *Escherichia coli*", Biotechnology and Bioengineering, vol. 38, pp. 1318–1324, 1991.

Masahiro Fukaya, "Cloning of Genes Responsible for acetic Acid Resistance in Acetobacter aceti", Journal of Bacreriology, pp. 2096–2104, Apr. 1990.

Seo, et al, "Glucose–Limited Fed–Batch Culture of *Escherica coli* for Production of Recombinant Human Interleukin–2 with the DO–Stat Method", Journal of Fermentation and Bioengineering, vol. 74, No. 3, pp. 196–198, 1992.

*Primary Examiner*—Nancy Degen
*Attorney, Agent, or Firm*—Oblon, Spivak, McClelland, Maier & Neustadt, P.C.

[57] ABSTRACT

The invention relates to a process for producing a desired substance by culturing a transformant in a medium until the desired substance is accumulated in the culture and then recovering the desired substance, the transformant being obtained by transforming an acetic acid-resistant microorganism of the genus Escherichia with a recombinant plasmid carrying a gene involved in production of the desired substance. The present process enables cells to be cultured easily at high density while the desired substance can be efficiently produced.

5 Claims, No Drawings

PROCESS FOR PRODUCING A SUBSTANCE

This application is a continuation of application Ser. No. 08/314,297, filed on Sep. 30, 1994, now abandoned.

FIELD OF THE INVENTION

The present invention relates to a process for efficiently producing a desired substance, and in particular to a process for producing a desired substance by culturing a transformant in which the genetic information involved in the production of the desired substance has been introduced into an acetic acid-resistant microorganism belonging to the genus Escherichia as a recipient.

BACKGROUND OF THE INVENTION

In the case of the production of a desired substance by *E. coli*, the culture of cells at high density is a useful means from the standpoint of the effective running of a fermentor and the efficient recovery of a product, as well as for an improvement in the yield of the product. In the case of *E. coli*, however, high-density culture has been difficult because the growth of the cells is inhibited in a medium with significant accumulation of acetic acid resulting from the metabolism of nutrient substances. To solve this problem, there are known a dialysis culture method [Journal of General Microbiology, 103, 345 (1977)] and a membrane cell recycle culture method [Biotechnology and Bioengineering, 36, 330 (1990)] of removing acetic acid from a culture system by dialysis or filtration of a liquid medium. Reports have also been made of a culture method of decreasing the formation of acetic acid by the supply of pure oxygen for maintaining a high concentration of dissolved oxygen in a liquid medium [Agricultural and Biological Chemistry, 53, 2115 (1989)] and a method of decreasing the accumulation of acetic acid by maintaining glucose at a low concentration in a liquid medium [Journal of Fermentation and Bioengineering, 74, 196 (1992)]. However, these methods cannot be said to be industrially advantageous because of the need for a special apparatus and the problem of complex maintenance and control of such apparatus.

Although a report has been made of a method for decreasing the ability of a microorganism to produce acetic acid by conferring sodium fluoroacetate resistance on the microorganism so that the enzyme activities in the pathway of acetic acid biosynthesis are lowered or deleted (Japanese Patent Publication No. 502065/90, European Patent Publication No. 316229), there exist disadvantages such as accumulation of pyruvic acid and lactic acid [Biotechnology and Bioengineering, 38, 1318 (1991)].

Some microorganisms belonging to the genera Acetobacter and Gluconobacter are known to be acetic acid-resistant [J. Bacteriology, 172, 2096–2104(1990)], but none is known of the acetic acid-resistant microorganism belonging to the genus Escherichia or the method of producing a desired substance by the use of said microorganism as a recipient.

SUMMARY OF THE INVENTION

The present invention provides a process for producing a substance which comprises culturing a microorganism in a medium until the desired substance is accumulated in the culture and then recovering the desired substance therefrom, wherein said microorganism is a transformant constructed by transformation of an acetic acid-resistant microorganism of the genus Escherichia with a recombinant plasmid carrying a gene involved in the production of the desired substance, as well as an acetic acid-resistant microorganism of the genus Escherichia useful as a recipient.

DETAILED DESCRIPTION OF THE INVENTION

As the recipient used in the invention, any microorganism is appropriate so long as it belongs to the genus Escherichia with resistance to acetic acid.

The term "resistance" refers to the ability of a microorganism to grow at the concentration of acetic acid at which the parent strain cannot grow.

The following examples illustrate transformants capable of growing in the presence of 150 mM acetic acid at which concentration the parent strain cannot grow, but any bacterial strain can be used so long as it is more resistant to acetic acid than the parent strain.

For preparation of such an acetic acid-resistant strain, a microorganism of the genus Escherichia for conventional use in the production of a desired substance is subjected to a conventionally used mutation treatment, followed by being spread onto a suitable agar plate medium containing acetic acid at the concentration at which the parent strain cannot grow, and the mutant which grows on the medium is then cultured under shaking in a suitable liquid medium containing acetic acid so that the growth of the cells is measured for the selection of an acetic acid-resistant strain with higher growth than that of the parent strain.

As more specific procedures, a microorganism of the genus Escherichia for conventional use in the production of a desired substance is subjected to a conventional mutation treatment, for example with a mutagen such as N-methyl-N'-nitro-N-nitrosoguanidine etc. or by UV irradiation, γ ray irradiation, etc., and the treated cells are diluted to an appropriate concentration and cultured on a suitable agar plate medium containing the concentration of acetic acid (150 mM) at which the parent strain cannot grow, to yield colonies which in turn are separated as mutants.

As the parent strain, mention may be made of any microorganism belonging to the genus Escherichia for conventional use in production of a desired substance, preferably *Escherichia coli*. Examples are *E. coli* strains such as MM294, MC1000, MC1061, LE392, W3110, JM105, JM109, XL1-Blue, DH1, DH5 α [J. Sambrook, E. F. Fritsch, T. Maniatis (1989) Molecular Cloning, 2nd Edition, Cold Spring Harbor Laboratory Press and T. J. Shilhav, M. L. Berman, L. W. Enquist (1984) Experiments with Gene Fusions, Cold Spring Harbor Laboratory Press].

To obtain the mutant of the present invention, the resulting mutants are cultured in a suitable liquid medium and the mutants which grow more abundantly and cause less decrease in pH of the culture medium, as compared with the parent strain, are selected.

As the mutants thus obtained, mention is made of *E. coli* HN0020 strain, *E. coli* HN0074 strain and *E. coli* HN0124 strain. All these bacterial strains are sensitive to fluoroacetic acid. Said bacterial strains were deposited respectively as FERM BP-4426, FERM BP-4425 and FERM BP-4427 with the National Institute of Bioscience and Human-Technology, Agency of Industrial Science and Technology, Japan, on Sep. 28, 1993, under the Budapest Treaty.

Even under culture conditions enabling the parent strain to produce a vast amount of acetic acid, the mutant of the invention produces a smaller amount of acetic acid than the parent strain, and the pH of the culture medium of the mutant is less decreased than that of the parent strain. Thus it is considered that pyruvic acid and lactic acid are accumulated in the culture in smaller amounts. Owing to the use of the mutant of the invention, therefore, cells can be easily cultured at high density without requiring any special culture apparatus or any complex techniques for the control of culture.

The mutant thus obtained is then transformed as a recipient with a recombinant plasmid in which a gene involved in production of a desired substance has been inserted into a vector, and the transformant can be cultured in a medium to produce the desired substance.

Using a microoraganism containing a recombinant plasmid carrying a cloned gene involved in the production of a desired substance, the process of the present invention can be widely applied to any desired substance. Examples of the desired substance are enzymes such as uricase and acetylpolyamineamide hydrolase, etc., physiologically active peptides such as $^{13}$Leu-motilin and human granulocyte colony-stimulating factor (G-CSF) etc., amino acids such as threonine etc., nucleic acid related substances such as flavin adenine dinucleotide etc., vitamins such as biotin etc. and pigments such as carotenoid etc.

Isolation of a gene involved in the production of a desired substance from the chromosome of a microorganism capable of producing the substance can be effected according to a conventional method described in e.g. Current Topics in Microbiology and Immunology, 96 (1982).

The gene thus obtained is inserted into a suitable vector for construction of a recombinant plasmid. As the vector, any vector is appropriate so long as a microorganism belonging to the genus Escherichia can be used as the recipient.

The gene is inserted into the vector in a usual manner, for example by cleaving the chromosomal DNA and vector DNA with suitable restriction enzymes and then ligating both DNAs by the action of DNA ligase.

As the recombinant plasmid, mention is made of the recombinant plasmid pUT118 carrying a gene involved in the production of uricase (European Patent Publication No. 545688), the recombinant plasmid ptrcNMAPH carrying a gene involved in the production of acetylpolyamineamide hydrolase (Japanese Published Unexamined Patent Application No. 71489/92), the recombinant plasmid pMTOI4 carrying a gene involved in production of $^{13}$Leu-motilin (Japanese Published Unexamined Patent Application No. 71195/88), the recombinant plasmid pCfBD28 carrying a gene involved in the production of G-CSF (Japanese Published Unexamined Patent Application No. 267292/88), and the recombinant plasmid pEthrl carrying a gene involved in the biosynthesis of threonine (Japanese Published Unexamined Patent Application No. 30693/85).

The recipient is transformed with a variety of the resulting recombinant plasmids in a conventional method described in e.g. Molecular Cloning, 2nd Edition.

As the transformant capable of producing a desired substance, mention may be made of $E.$ $coli$ strains such as HN0021, HN0027, HN0028, HN0075, HN0125 and HN0310.

The transformant can be cultured in a medium containing carbon sources, nitrogen sources, inorganic substances, etc., under aerobic conditions while temperature, pH etc. are controlled.

Any carbon source may be used so long as the microorganism can assimilate it. Examples are carbohydrates such as glucose, fructose, sucrose, molasses, blackstrap molasses, starch hydrolysates, etc.; alcohols such as ethanol, glycerol, sorbitol, etc.; organic acids such as pyruvic acid, lactic acid, acetic acid, etc.; and amino acids such as glycine, alanine, glutamic acid, aspartic acid, etc.

As the nitrogen source, mention may be made of ammonia, various inorganic and organic ammonium salts such as ammonium chloride, ammonium sulfate, ammonium nitrate, ammonium carbonate, ammonium acetate, ammonium phosphate, etc.; nitrogen-containing organic substances such as urea, peptone, NZ amine, meat extract, yeast extract, corn steep liquor, casein hydrolysates, fish meal or its digested products; and various amino acids such as glycine, glutamic acid, etc.

As the inorganic compound, mention may be made of potassium dihydrogen phosphate, dipotassium hydrogen phosphate, magnesium sulfate, magnesium phosphate, sodium chloride, ferrous sulfate, manganese sulfate, zinc sulfate, calcium carbonate, etc.

If required by the microorganisms for their growth, nutrients such as amino acids, nucleic acids, vitamins, etc., are added in a suitable amount.

Culture is carried out at 25°–42° C. for 1–48 hours under aerobic conditions, for example by shaking culture or by agitation submerged culture. The pH of the medium is preferably maintained around neutrality by addition of aqueous ammonia, a urea solution, a sodium hydroxide solution, etc.

The object substance produced according to the culture described above is quantitatively determined in the following manner. At the end of culture, $E.$ $coli$ cells are collected for example by centrifugation and suspended in an appropriate buffer. According to the method as described by Laemmli et al. (U. K. Laemmli, Nature, 227, 680 (1970)), the suspension or alternatively a cell-free extract prepared therefrom is subjected to electrophoresis on SDS-polyacrylamide gel, followed by being stained with Coomassie Brilliant Blue R-250 so that the object substance can be quantitatively determined on a chromatoscanner. The preparation of a cell-free extract involves disrupting cells by means of sonication, grinding treatment with glass beads, treatment with French press, etc. If the object substance possesses an activity, it may be quantitatively determined by measurement of the activity in the cell-free extract.

According to the present process for producing a desired substance by an $E.$ $coli$ recombinant, cells can be cultured easily at high density simultaneously with efficient production of a desired substance.

EXAMPLES

Hereinafter, the present invention is described in detail.

Example 1

Construction of an acetic acid-resistant strain from $E.$ $coli$ MM294 strain $E.$ $coli$ MM294 strain was inoculated into 30 ml LB medium in 30 ml Erlenmeyer flask (10 g/l Bacto-trypton, 5 g/l Bacto-yeast extract, 5 g/l NaCl) and cultured at 37° C. for 3 hours under shaking to give cells at the logarithmic growth phase which were then recovered by centrifugation at 4° C. at 10,000 rpm for 10 min. with a refrigerating centrifuge RD-20IV (Rotor No. 4) manufactured by Tommy Seiko. Co., Ltd. For mutation, the cells were suspended in TM buffer [6.057 g/l tris(hydroxymethyl)aminomethane (hereinafter referred to as "Tris"), 5. 804 g/l maleic acid, 0.1 g/l MgSO$_4$.7H$_2$O, 1 g/l (NH$_4$)$_2$SO$_4$, 0.5 g/l sodium citrate, pH 6.0] containing 0.5 mg/ml N-methyl-N'-nitro-N-nitrosoguanidine so that the cells were mutated at 35° C. for 60 min. under slow shaking. The cells were collected, washed and suspended at a concentration of approximately 10$_5$ cells/ml in sterilized water. This suspension, 0.1 ml per application, was spread onto a plate medium composed of MCGA medium, [5 g/l glucose, 11.562 g/l ammonium acetate (150 mM acetic acid), 15.14 g/l Na$_2$HPO$_4$.12H$_2$O, 3 g/l KH$_2$PO$_4$, 5 g/l NaCl, 1 g/l NH$_4$Cl, 0.24 g/l MgSO$_4$.7H$_2$O, 5 g/l casamino acid, 4 µg/ml vitamin B$_1$] containing 1.5% agar (hereinafter referred to as "MCGA agar medium"), and the cells were cultured at 35° C. for 2 days to give colonies which were then isolated as mutants. The mutants were inoculated onto 10 ml MCGA medium in a test tube (diameter:24 mm) and then cultured at 30° C. for 24 hours under shaking. At the end of culture, each culture was measured for turbidity ($OD_{550}$) at an wavelength of 550 nm with a spectrophotometer. A mutant with higher growth than that of the parent strain MM294 was selected.

Then, this mutant was inoculated into 10 ml MCG medium (10 g/l glucose, 15.14 g/l $Na_2HPO_4.12H_2O$, 3 g/l $KH_2PO_4$, 5 g/l NaCl, 1 g/l $NH_4Cl$, 0.24 g/l $MgSO_4.7H_2O$, 5 g/l casamino acid, 4 µg/ml vitamin $B_1$) in a test tube (diameter:24 mm) and cultured at 30° C. for 24 hours under shaking. At the end of culture, a bacterial strain which grew abundantly and gave less decrease in pH of the medium was selected and designated E. coli HN0020 strain.

Table 1 shows the abilities of the parent MM294 strain and HN0020 strain to grow in MCGA liquid medium, and that HN0020 strain demonstrated higher growth than that of the parent strain.

TABLE 1

| | Growth in MCGA Medium | |
|---|---|---|
| growth | MM294 | HN0020 |
| $OD_{550}$ | 4.0 | 13.8 |

HN0020 strain was spread onto MCGA agar medium containing acetic acid at a predetermined concentration and cultured at 33° C. for 2 days for the evaluation of growth. The results are shown in Table 2. HN0020 strain could grow in MCGA agar medium even containing 150 mM acetic acid to demonstrate higher acetic acid-resistance than that of the parent strain.

TABLE 2

| | acetic acid content (mM) in MCGA medium | | |
|---|---|---|---|
| bacterial strain | 50 | 100 | 150 |
| MM294 | + | + | − |
| HN0020 | + | + | + |

+: growing
−: not growing

Growth of cells and the amount of acetic acid formed in MCG medium are set forth in Table 3.

MM294 and HN0020 strains were inoculated respectively into 10 ml MCG medium in a test tube (diameter:24 mm) and cultured at 30° C. for 24 hours under shaking. The accumulation of organic acids in the culture was analyzed by HPLC, and as a result, no organic acetic acid was found except for acetic acid and accumulation of acetic acid by HN0020 strain was less than that by the parent strain. As shown in Table 3, HN0020 strain demonstrated higher growth and less formation of acetic acid than the parent MM294 strain did.

TABLE 3

| | Formation of Acetic Acid in MCG Medium | | |
|---|---|---|---|
| bacterial strain | growth $OD_{550}$ | pH | acetic acid formation [g/l] |
| MM294 | 12.9 | 4.51 | 0.27 |
| HN0020 | 14.4 | 4.84 | 0.14 |

Example 2

Production of uricase by the acetic acid-resistant HN0020 strain

HN0020 strain obtained in Example 1 was transformed with the recombinant plasmid pUT118 for the expression of uricase (EP-A-545688). Competent cells of HN0020 strain were prepared in accordance with the method described in Journal of Molecular Biology, 166, 557 (1983). For transformation, 210 µl of the competent cells were mixed with 1 µl of pUT118 solution, then allowed to stand on ice for 30 min. and heated at 42° C. for 90 sec., followed by being kept on ice for 2 min. 800 µl of SOC medium (2% Bacto-trypton, 0.5 % Bacto-yeast extract, 10 mM NaCl, 2.5 mM KCl, 10 mM $MgCl_2$, 10 mM $MgSO_4$, 20 mM glucose) was added thereto and the cells were cultured at 37° C. for 1 hour under shaking. The cells, 100 µl per application, were spread onto an LB agar plate medium containing 50 µg/ml ampicillin. After incubation overnight at 37° C., the colonies formed were obtained as transformants. A plasmid was then purified therefrom in a usual manner. This plasmid was identified as pUT118 by structural analysis, and the recombinant E. coli was designated HN0021 strain.

(1) Culture of HN0021 strain in a flask

HN0021 strain was inoculated into 30 ml of MCG medium in 300 ml Erlenmeyer flask and cultured at 33° C. for 24 hours under shaking, and the cells were recovered by centrifugation at 10,000 rpm for 10 min. The cells were then suspended in 3 ml of PBS buffer (8 g/l NaCl, 0.2 g/l KCl, 1.25 g/l $Na_2HPO_4.12H_2O$, 0.2 g/l $KH_2PO_4$) and disrupted with a sonicator (Branson Co., Ltd., CELL DISRUPTOR 200). The cell solution thus obtained was centrifuged at 14,000 rpm for 15 min. to yield a supernatant as a cell-free extract. The production of uricase was determined as the activity of uricase in the cell-free extract.

For determination of the activity of uricase, the decrease in UV absorbance (293 nm) of the substrate uric acid was monitored in the following manner. The cell-free extract diluted to 0.15 µg/ml protein including uricase was added to 3 ml of a reaction solution [50 mM borate buffer, pH 8.5, 125 µM uric acid], and the mixture was allowed to react at 25° C. for 3 min. The change in absorbance (ΔOD) at 293 nm during reaction was monitored, and its uricase unit (U) is calculated according to the following equation. 1 U refers to the amount of uricase with which 1 µmole of uric acid is decomposed for 1 min. under the conditions described above.

U=(ΔOD×3×degree of dilution of enzyme solution)/(12.6× 3)

12.6: millimolar molecular extinction coefficient of uric acid ($cm^2$/ µ mole)

As can be seen in Table 4, the use of HN0020 strain as a recipient resulted in enhanced production of increase as compared with MM294 strain.

TABLE 4

| Growth in MCG Medium and Production of Uricase | | | |
|---|---|---|---|
| bacterial strain | growth [$OD_{550}$] | pH | uricase production [U/ml culture] |
| MM294/pUT118 | 13.1 | 4.6 | 39.1 |
| HN0020/pUT118 (HN0021) | 12.0 | 6.2 | 74.0 |

(2) Culture of HN0021 strain in a jar fermentor

For the culture of HN0021 strain in a jar fermentor, the high-density culture method (Biotechnology and Bioengineering, 17, 227 (1975)) is preferably used. For this method, 50 µg/ml ampicillin was added to every culture medium for the stable maintenance of a plasmid in recombinant E. coli. High-density culture was carried out in the following manner. In pre-culture, HN0021 strain was inoculated into 100 ml of medium A containing 1% glucose in 1 litter Erlenmeyer flask and cultured at 30° C. for 16 hours under shaking.

Separately, 1.8 l of medium A was introduced into 5 l fermentor and sterilized at 120° C. for 20 min., followed by addition of 100 ml of sterilized solution containing 10% glucose, 2.4% $MgSO_4 \cdot 7H_2O$, and 0.4% vitamin $B_1$, into which the pre-cultured HN0021 strain was then inoculated.

TABLE 5

| Medium A | |
|---|---|
| 7.0 g/l | $Na_2HPO_4 \cdot 12H_2O$ |
| 4.0 g/l | $KH_2PO_4$ |
| 4.0 g/l | $K_2HPO_4$ |
| 1.2 g/l | $(NH_4)_2SO_4$ |
| 0.2 g/l | $NH_4Cl$ |
| 4.0 g/l | Bacto-yeast extract |
| 40.0 mg/l | $FeSO_4 \cdot 7H_2O$ |
| 40.0 mg/l | $CaCl_2 \cdot 2H_2O$ |
| 10.0 mg/l | $MnSO_4 \cdot nH_2O$ |
| 10.0 mg/l | $AlCl_3 \cdot 6H_2O$ |
| 4.0 mg/l | $CoCl_2 \cdot 6H_2O$ |
| 2.0 mg/l | $ZnSO_4 \cdot 7H_2O$ |
| 2.0 mg/l | $Na_2MoO_4 \cdot 2H_2O$ |
| 1.0 mg/l | $CuSO_4 \cdot 5H_2O$ |
| 0.5 mg/l | $H_3BO_3$ |

Culture was conducted at 33° C. for 24 hours with agitation (500 rpm) and aeration (2 l/min.), while the medium was adjusted to pH 6.8 with 14% aqueous ammonia. 70% glucose was successively fed to the fermentor so as to maintain glucose at 0.5%, 1% or 2% in the medium. When the culture reached an $OD_{550}$ of 50 by growth, Medium B was added to Medium A at a ratio of 100 ml:1 litter.

TABLE 6

| Medium B (100 ml of medium B is added to 1 litter of medium A) | |
|---|---|
| 12.0 g/l | $KH_2PO_4$ |
| 12.0 g/l | $K_2HPO_4$ |
| 4.0 g/l | Bacto-yeast extract |
| 2.6 g/l | $MgSO_4 \cdot 7H_2O$ |
| 186.0 mg/l | $FeSO_4 \cdot 7H_2O$ |
| 186.0 mg/l | $CaCl_2 \cdot 2H_2O$ |
| 66.0 mg/l | $MnSO_4 \cdot nH_2O$ |
| 28.0 mg/l | $ZnSO_4 \cdot 7H_2O$ |
| 14.0 mg/l | $CoCl_2 \cdot 6H_2O$ |
| 5.0 mg/l | $CUSO_4 \cdot 5H_2O$ |
| 4.2 mg/l | $Na_2MoO_4 \cdot 2H_2O$ |

For quantitative determination of the acetic acid formed in the medium, the culture was centrifuged and the culture supernatant was analyzed by gas chromatography (Hitachi 236-50 type, column; PEG-6000 (SUPPORT: Chromosorb WAW), column length; 1 m, column temperature; 170° C., carrier gas; helium, flow rate; 60 ml/min., and detector; FID).

Table 7 shows the results of 24 hour culture. Where the parent MM294 strain was used as the recipient, a high amount of acetic acid was formed. On the other hand, less acetic acid was formed in every glucose concentration in the case of HN0021 strain where HN0020 strain was used as the recipient and the cells could be cultured at higher density. As the recipient, HN0020 strain brought about higher production of uricase than MM294 strain. Owing to the use of such an acetic acid-resistant strain as a recipient, therefore, it is possible to effect not only the culture of cells at higher density without any troublesome control of glucose concentration during culture, but also the efficient production of a higher amount of uricase in the culture.

TABLE 7

| | Growth of cells and Production of Uricase | | | |
|---|---|---|---|---|
| bacterial strain | controlled glucose conc. [%] | growth [$OD_{550}$] | acetic acid formed [g/l] | uricase prodn. [U/ml culture] |
| MM294/ pUT118 | 0.5 | 55.6 | 33.7 | 136.9 |
| | 1.0 | 50.8 | 21.9 | 81.1 |
| | 2.0 | 54.0 | 19.5 | 73.6 |
| HN0020/ pUT118 (HN0021) | 0.5 | 92.0 | 13.3 | 403.1 |
| | 1.0 | 94.0 | 10.8 | 338.1 |
| | 2.0 | 78.0 | 8.4 | 387.2 |

Example 3

Production of acetylpolyamineamide hydrolase by HN0020 strain

HN0020 strain obtained in Example 1 was transformed in the same manner as in Example 2 with the recombinant plasmid ptrcNMAPH for expression of acetylpolyamineamide hydrolase (Japanese Published Unexamined Patent Application No. 71489/92). A plasmid was isolated and purified from the transformant, and this plasmid was identified as ptrcNMAPH by structural analysis. The recombinant E. coli was designated HN0027 strain.

HN0027 strain was inoculated into 30 ml MCG medium in 300 ml Erlenmeyer flask and cultured at 28° C. for 24 hours under shaking, and the cells were recovered by centrifugation at 10,000 rpm for 10 min.

After the protein concentration of the cell-free extract was determined using a protein assay kit (Bio-Rad), the extract was adjusted to 0.2 mg/ml. This sample was added to the equal volume of a sample-treatment solution [20 ml aqueous solution containing 0.92 g SDS, 2 ml of β-mercaptoethanol, 4.0 g of glycerol, 0.3 g of Tris and 2 ml of 0.1% (W/V) Bromophenol Blue and adjusted to pH 6.8 with hydrochloric acid], and the sample solution was allowed to stand at 100° C. for 2 min. Then, 10 μl of the sample solution was loaded onto 14% polyacrylamide gel (14 cm×11 cm) and electrophoresed at 40 mA for 2 hours. After electrophoresis, the gel was stained for 3 hours in a gel-staining solution (0.25 g of Coomassie Brilliant Blue R250, 125 ml of methanol, 25 ml of acetic acid, 100 ml of water) and then decolored for 12 hours in a decoloring solution (100 ml of methanol, 100 ml of acetic acid, 800 ml of water). After decoloration, the polyacrylamide gel was monitored for absorbance at 560 nm with chromatoscanner CS-930 (Shimadzu), whereby the content of acetylpolyamineamide hydrolase in the cell-free extract was determined.

As shown in Table 8, the use of HN0020 strain as a recipient resulted in enhanced production of acetylpolyamineamide hydrolase as compared with MH294 strain.

TABLE 8

Growth of cells and Prodn. of Acetylpolyamineamide Hydrolase in MCG Medium

| bacterial strain | growth [OD$_{550}$] | pH | APH[1] content[2] |
|---|---|---|---|
| MM294/ptrcNMAPH | 12.9 | 4.9 | 14.9% |
| HN0020/ptrcNMAPH (HN0027) | 13.8 | 6.0 | 18.5% |

[1] APH: acetylpolyamineamide hydrolase
[2] Content in the total proteins of the cell-free extract

Example 4

Production of $^{13}$Leu-motilin by HN0020 strain

HN0020 strain obtained in Example 1 was transformed in the same manner as in Example 2 with the recombinant plasmid pMTOI4 for expression of $^{13}$Leu-motilin (Japanese Published Unexamined Patent Application No. 71195/88). A plasmid was isolated and purified from the transformant, and this plasmid was identified as pMTOI4 by structural analysis. The recombinant E. coli was designated HN0028 strain.

HN0028 strain was inoculated into 30 ml MCG medium in 300 ml Erlenmeyer flask and cultured at 35° C. for 24 hours under shaking, and the cells were recovered by centrifugation at 10,000 rpm for 10 min.

The cells thus obtained were suspended to a turbidity (OD$_{550}$) of 8.5 in a PBS buffer, and then the microorganism was disrupted by sonication. A sample prepared from the solution of the disrupted microorganism was electrophoresed on 14% polyacrylamide gel. After electrophoresis, the gel was stained so that the content of $^{13}$Leumotilin in the total proteins of the microorganism was determined with the chromatoscanner.

As shown in Table 9, the use of HN00020 strain as a recipient resulted in enhanced production of 13 Leu-motilin as compared with MM294 strain.

TABLE 9

Growth and Production of $^{13}$Leu-motilin in MCG Medium

| bacterial strain | growth [OD$_{550}$] | pH | $^{13}$Leu-motilin content[1] |
|---|---|---|---|
| MM294/pMTOI4 | 9.0 | 4.6 | 8.0% |
| HN0020/pMTOI4 (HN0028) | 11.8 | 4.9 | 12.7% |

[1] Content of $^{13}$Leu-motilin in total bacterial proteins

Example 5

Construction of an acetic acid-resistant strain from E. coli MC1000 strain

According to the same manner as in Example 1, a mutant was obtained from E. coli MC1000 strain and designated HN0074 strain.

HN0074 strain was inoculated onto MCGA agar medium containing acetic acid at a predetermined concentration and cultured at 33° C. for 2 days. The results are shown in Table 10. HN0074 strain could grow in MCGA agar medium even containing 150 mM acetic acid to demonstrate higher acetic acid-resistance than that of the parent strain.

TABLE 10

| bacterial strain | acetic acid content (mM) in MCGA medium | | |
|---|---|---|---|
| | 50 | 100 | 150 |
| MC1000 | + | + | − |
| HN0074 | + | + | + |

+: growing
−: not growing

MC1000 and HN0074 strains were inoculated respectively into 10 ml MCG medium in a test tube (diameter: 24 mm) and cultured at 30° C. for 24 hours under shaking, and the amounts of acetic acid produced were compared. The results are shown in Table 11. The acetic acid-resistant HN0074 strain showed higher growth with less formation of acetic acid than the parent MC1000 strain did.

TABLE 11

Formation of Acetic Acid in MCG Medium

| bacterial strain | growth [OD$_{550}$] | pH | acetic acid formation [g/l] |
|---|---|---|---|
| MC1000 | 6.5 | 4.88 | 0.44 |
| HN0074 | 11.4 | 5.00 | 0.33 |

Example 6

Production of uricase by HN0074 strain

HN0074 strain obtained in Example 5 was transformed in the same manner as in Example 2 with the recombinant plasmid pUT118 for expression of uricase. A plasmid was isolated and purified from the transformant, and this plasmid was identified as pUT118 by structural analysis. The recombinant E. coli was designated HN0075 strain.

HN0075 strain was inoculated into 30 ml MCG medium in 300 ml Erlenmeyer flask and cultured at 33° C. for 24 hours under shaking, and the cells were recovered by centrifugation at 10,000 rpm for 10 min. A cell-free extract was obtained from the cells, and production of uricase was determined. As shown in Table 12, the growth of HN0075 strain was higher than that of the recombinant E. coli from MC1000 strain as the recipient, and the use of HN0074 strain as a recipient resulted in enhanced production of uricase as compared with MC1000 strain.

TABLE 12

Growth of cells and Production of Uricase in MCG Medium

| bacterial strain | growth [OD$_{550}$] | pH | uricase production [U/ml culture] |
|---|---|---|---|
| MC1000/pUT118 | 7.2 | 4.5 | 13.2 |
| HN0074/pUT118 (HN0075) | 13.0 | 6.4 | 26.2 |

Example 7

Construction of an acetic acid-resistant strain from E. coli NY49 strain

According to the same manner as in Example 1, a mutant was obtained from E. coli NY 49 strain and designated HN0124 strain.

HN0124 strain was inoculated onto MCGA agar medium containing a pre-determined concentration and cultured at 33° C. for 2 days for the evaluation of growth. The results are shown in Table 13. HN0124 strain could grow on MCGA agar medium even containing 150 mM acetic acid to show higher acetic acid-resistance than that of the parent strain.

TABLE 13

| bacterial strain | acetic acid content (mM) in MCGA medium | | |
|---|---|---|---|
| | 50 | 100 | 150 |
| NY49 | + | + | − |
| HN0124 | + | + | + |

+: growing
−: not growing

NY49 and HN0124 strains were inoculated respectively into 10 ml MCG medium in a test tube (diameter: 24 mm) and cultured at 30° C. for 24 hours under shaking, and the amounts of acetic acid formed therein were compared. The results are shown in Table 14. The acetic acid-resistant HN0124 strain grew more abundantly and caused less formation of acetic acid than the parent NY49 strain did.

TABLE 14

Formation of Acetic Acid in MCG Medium

| bacterial strain | growth $OD_{550}$ | pH | acetic acid formation [g/l] |
|---|---|---|---|
| NY49 | 12.5 | 6.3 | 0.2 |
| HN0124 | 13.0 | 6.4 | 0.0 |

Example 8

Production of human granulocyte colony-stimulating factor by HN0124 strain

HN0124 strain obtained in Example 7 was transformed in the same manner as in Example 2 with the recombinant plasmid pCfBD28 for expression of human granulocyte colony-stimulating factor (G-CSF) (Japanese Published Unexamined Patent Application No. 267292/88). A plasmid was isolated and purified from the transformant, and this plasmid was identified as pCfBD28 by structural analysis. The recombinant E. coli was designated HN0125 strain.

The recombinant E. coli HN0125 strain was inoculated into 30 ml MCG medium in 300 ml Erlenmeyer flask and cultured at 33° C. for 24 hours under shaking, and the cells were recovered by centrifugation at 10,000 rpm for 10 min. A cell-free extract was obtained from the cells and the amount of granulocyte colony-stimulating factor produced therein was determined. As shown in Table 15, the growth of HN0125 strain was higher than that of the recombinant E. coli from NY49 strain as the recipient, and the use of HN0124 strain as a recipient resulted in enhanced production of granulocyte colony-stimulating factor as compared with NY49 strain.

TABLE 15

Growth of cells and Prodn. of Granulocyte Colony-Stimulating Factor in MCG medium

| bacterial strain | growth $[OD_{550}]$ | pH | G-CSF production[1] [%] |
|---|---|---|---|
| NY49/pCfBD28 | 9.6 | 4.6 | 5.8 |
| HN0124/pCfBD28 (HN0125) | 10.4 | 4.8 | 10.3 |

[1] Content in the total proteins of the cell-free extract

Example 9

Production of L-threonine by HN0020 strain

HN0020 strain obtained in Example 1 was transformed in the same manner as in Example 2 with the recombinant plasmid pEthrl carrying an E. coli-derived gene involved in the biosynthesis of L-threonine (Japanese Published Unexamined Patent Application No. 30693/85). A plasmid was isolated and purified from the transformant in a usual manner, and this plasmid was identified as pEthrl by structural analysis. The recombinant E. coli was designated HN0310 strain. HN0310 strain was placed in 300 ml Erlenmeyer flask with 30 ml of MCGG medium having the concentration of glucose increased to 20 g/l in the MCG medium composition. The microorganism was cultured at 35 ° C. for 48 hours under shaking and then centrifuged at 10,000 rpm for 10 min. to give a culture supernatant.

For quantitative determination of the l-threonine produced, the culture supernatant was analyzed with an amino acid analyzer (a product of Nippon Bunko Co., Ltd., amino acid analysis system by high performance liquid Chromatography).

As shown if Table 16, the use of HN0020 strain as a recipient resulted in enhanced production of uricase as compared with mm294 strain.

TABLE 16

Growth of cells and Production of L-Threonine in MCGG Medium

| bacterial strain | growth $[OD_{550}]$ | pH | L-threonine production [g/l] |
|---|---|---|---|
| MM294/pEthr1 | 13.0 | 4.1 | 1.4 |
| HN0020/pEthr1 (HN0310) | 14.2 | 4.4 | 3.7 |

What is claimed is:

1. A process for producing a substance, which comprises culturing a microorganism in a medium until the substance is accumulated in a culture, and recovering the substance therefrom, wherein said microorganism is a transformant constructed by transformation of an acetic acid-resistant mutant belonging to the genus Escherichia with a recombinant plasmid carrying a gene involved in the production of the substance.

2. The process according to claim 1, wherein the substance is an enzyme, a physiologically active peptide, an amino acid, a nucleic acid-related substance, a vitamin or a pigment.

3. The process according to claim 1, wherein the substance is uricase, acetylpolyamineamide hydrolase, [13]Leumotilin, human granulocyte colony-stimulating factor, threonine, flavin adenine dinucleotide, biotin or carotenoid.

4. A mutant microorganism which is resistant to acetic acid and belongs to the genus Escherichia.

5. The microorganism as claimed in claim 4, which is selected from the group consisting of *Escherichia coli* FERM BP-4425, *Escherichia coli* FERM BP-4426 and *Escherichia coli* FERM BP-4427.

* * * * *